(12) United States Patent
Shibata et al.

(10) Patent No.: US 7,658,494 B2
(45) Date of Patent: Feb. 9, 2010

(54) FUNDUS CAMERA

(75) Inventors: Naohisa Shibata, Gamagori (JP);
Masaaki Hanebuchi, Nukata-gun (JP);
Tsuguo Nanjo, Toyohashi (JP)

(73) Assignee: Nidek Co., Ltd, Gamagori (JP)

( * ) Notice: Subject to any disclaimer, the term of this patent is extended or adjusted under 35 U.S.C. 154(b) by 76 days.

(21) Appl. No.: 12/155,435

(22) Filed: Jun. 4, 2008

(65) Prior Publication Data

US 2008/0316426 A1    Dec. 25, 2008

(30) Foreign Application Priority Data

Jun. 4, 2007    (JP) ............................. 2007-148686

(51) Int. Cl.
*A61B 3/14* (2006.01)
*A61B 3/10* (2006.01)

(52) U.S. Cl. ..................... 351/206; 351/205; 351/208; 351/211

(58) Field of Classification Search .......... 351/205–246
See application file for complete search history.

(56) References Cited

U.S. PATENT DOCUMENTS

| 6,478,424 B1 | 11/2002 | Grinvald et al. ............. 351/206 |
| 7,331,670 B2 * | 2/2008 | Ichikawa .................... 351/206 |
| 7,354,154 B2 * | 4/2008 | Matsumoto ................. 351/206 |
| 2005/0117115 A1 | 6/2005 | Ichikawa ..................... 351/206 |
| 2005/0270485 A1 | 12/2005 | Matsumoto .................. 351/206 |
| 2007/0139613 A1 | 6/2007 | Tanifuji et al. .............. 351/206 |
| 2007/0188707 A1 | 8/2007 | Nanjo ......................... 351/206 |

FOREIGN PATENT DOCUMENTS

| JP | A-2002-521115 | 7/2002 |
| JP | A-2005-160550 | 6/2005 |
| JP | A-2005-342283 | 12/2005 |
| JP | A-2006-136379 | 6/2006 |
| JP | A-2007-202952 | 8/2007 |
| WO | WO 00/06015 | 2/2000 |
| WO | WO 2005/084526 A1 | 9/2005 |

* cited by examiner

*Primary Examiner*—Mohammed Hasan
(74) *Attorney, Agent, or Firm*—Oliff & Berridge, PLC

(57) ABSTRACT

A fundus camera having a function of measuring a retinal function, capable of picking up (obtaining) a sharp color image of a fundus suitable for a fundus examination and measuring a retinal function with high accuracy comprises an illumination optical system comprising a visible light source, an image-pickup optical system comprising an image-pickup element, a mode selection switch for performing switching between a fundus photographing mode and a retinal function measurement mode based on variance of an intrinsic signal of a retina made by retinal stimulation, and a control unit which controls the optical systems, wherein the unit lowers, when the retinal function measurement mode is selected, illumination intensity of the illumination optical system per unit time in illuminating the fundus than that in picking up the color fundus image, and controls the element to pick up first and second visible fundus images at different points in time.

10 Claims, 2 Drawing Sheets

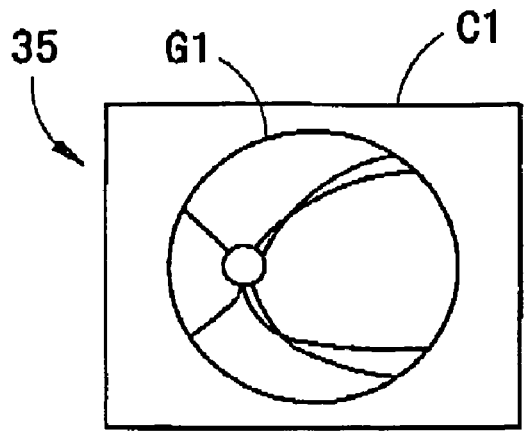
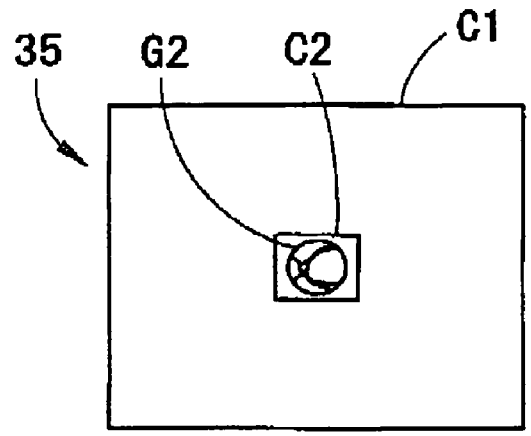
FIG. 2A    FIG. 2B
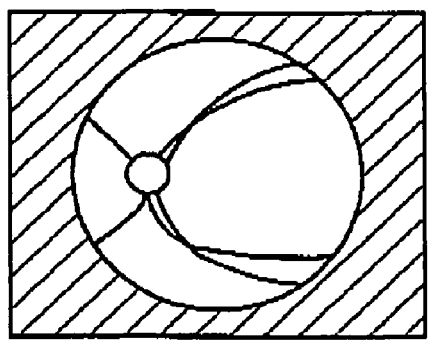
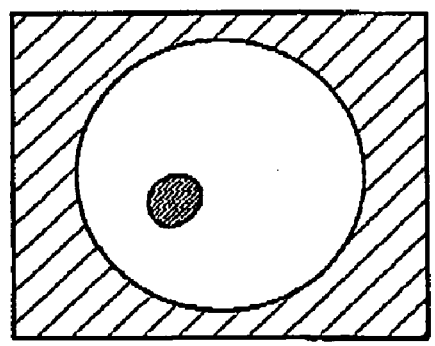
FIG. 3A    FIG. 3B

FUNDUS CAMERA

BACKGROUND OF THE INVENTION

1. Field of the Invention

The present invention relates to a fundus camera which photographs a fundus of an examinee's eye.

2. Description of Related Art

There is known a fundus camera which picks up a color image of a fundus of an examinee's eye by illuminating the fundus with visible flash light and photo-receiving reflection light from the fundus on an image-pickup element and displays the picked-up color fundus image on a monitor (see U.S. Pat. No. 7,331,670 corresponding to Japanese Patent Application Unexamined Publication No. 2005-160550).

In addition, an apparatus for measuring a retinal function is proposed in recent years which includes an optical system for illuminating a fundus of an examinee's eye with infrared light and photo-receiving reflection light from the fundus on an image-pickup element and an optical system for irradiating the fundus with stimulating light which induces a functional response from a retina of the eye (retinal stimulation means), picks up by the image-pickup element infrared images of the fundus before and after irradiating the stimulating light, and measures a retinal function of the eye by obtaining an intrinsic signal from the retina based on variance of reflectance between the picked-up infrared fundus images (see WO 2005/084526).

Both the fundus camera and the retinal function measurement apparatus are apparatuses which pick up a fundus image, so that if those apparatuses are combined, it is preferable that the above-described facilities of those apparatuses are integrated into respective systems in view of efficiency, space saving and other objectives. In order to achieve the integration, it is necessary for the combined apparatus to satisfy two conditions that a high-resolution and sharp color fundus image suitable for a fundus examination should be picked up (obtained) and a retinal function should be measured with high accuracy.

SUMMARY OF THE INVENTION

An object of the invention is to overcome the problems described above and to provide a fundus camera having a function of measuring a retinal function, which is capable of picking up (obtaining) a sharp color image of a fundus of an examinee's eye suitable for a fundus examination and measuring a retinal function of the eye with high accuracy.

To achieve the objects and in accordance with the purpose of the present invention, a fundus camera comprises an illumination optical system comprising a visible light source, for illuminating a fundus of an examinee's eye with visible light from the light source, an image-pickup optical system comprising an image-pickup element, for photo-receiving reflection light from the fundus illuminated by the illumination optical system and picking up an image of the fundus, a mode selection switch with which switching between a fundus photographing mode of picking up a normal color fundus image and a retinal function measurement mode of measuring a retinal function of the eye based on variance of an intrinsic signal of a retina of the eye made by retinal stimulation is performed, and a control unit arranged to control the illumination optical system and the image-pickup optical system, wherein the control unit lowers, when the retinal function measurement mode is selected, illumination intensity of the illumination optical system per unit time in illuminating the fundus by the illumination optical system than illumination intensity per unit time in picking up the color fundus image, and controls the image-pickup element to pick up a first visible fundus image and a second visible fundus image which are picked up at different points in time.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate an embodiment of the present invention and, together with the description, serve to explain the objects, advantages and principles of the invention. In the drawings.

FIGS. 2A and 2B are views showing examples of fundus images which are obtained when an image forming magnification on an image-pickup element is varied.

FIG. 3A is a view showing an example in displaying a normal color fundus image on a monitor, and FIG. 3B is a view showing an example in displaying a result of measurement of a retinal function on the monitor.

DETAILED DESCRIPTION OF THE PREFERRED EMBODIMENTS

Figure 1:
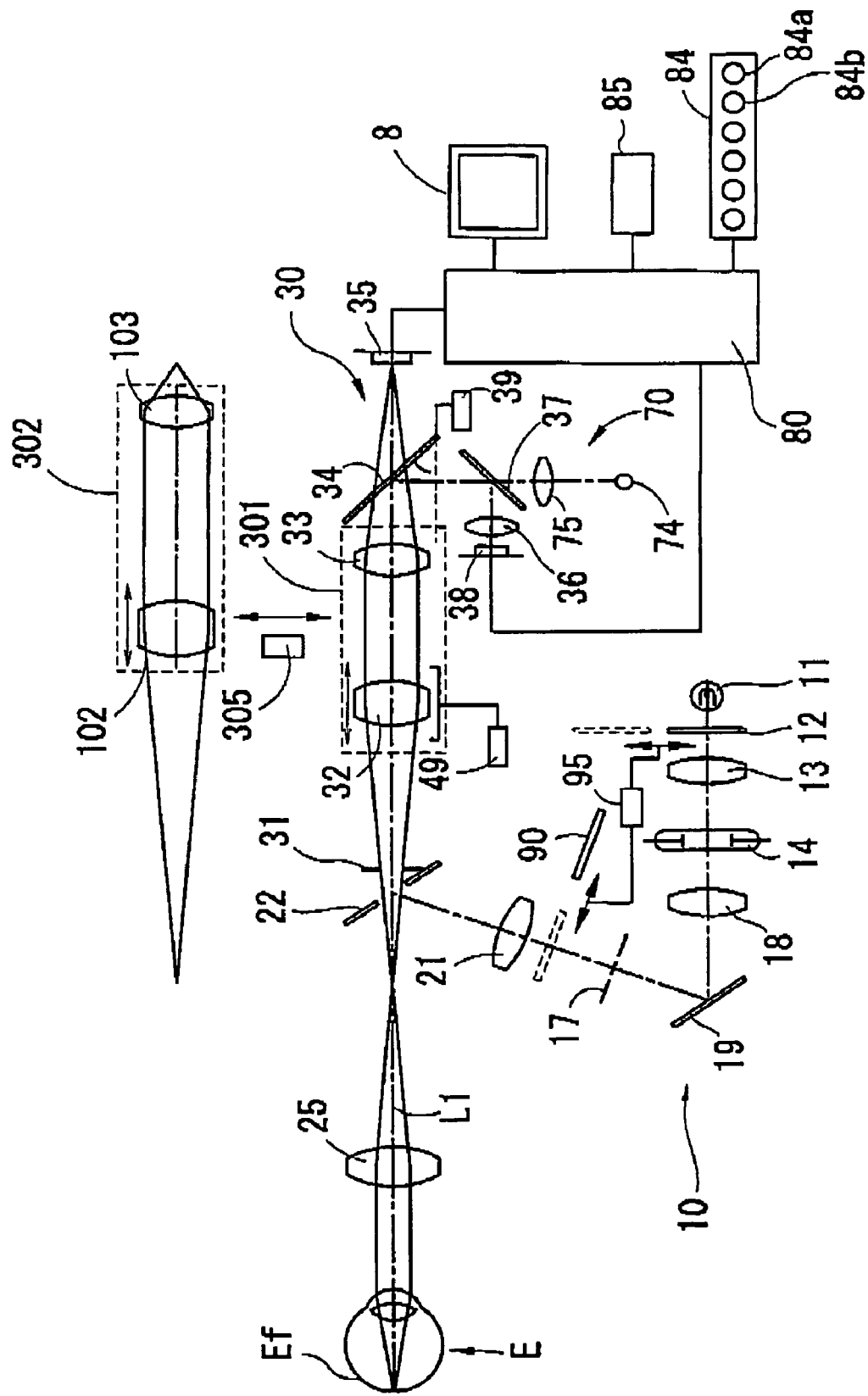
FIG. 1 is a view showing a schematic configuration of an optical system and a control system of a fundus camera having a function of measuring a retinal function according to a preferred embodiment of the present invention.

A detailed description of a fundus camera according to a preferred embodiment of the present invention is provided below with reference to the accompanying drawings. FIG. 1 is a view showing a schematic configuration of an optical system and a control system of the fundus camera having a function of measuring a retinal function according to the preferred embodiment of the present invention. The optical system comprises an illumination optical system 10 for illuminating a fundus Ef of an examinee's eye E, an image-pickup optical system 30 for photo-receiving reflection light from the fundus Ef illuminated by the illumination optical system 10 and picking up (obtaining) an image of the fundus Ef (a fundus image), and a fixation target presenting optical system 70 for fixating the eye E.

The illumination optical system 10 comprises an illumination optical system for photographing and an illumination optical system for observation. The illumination optical system for photographing comprises an illumination light source 14 for photographing such as a flash lamp, a relay lens 18, a total reflection mirror 19, a ring-slit plate 17, a relay lens 21, an apertured mirror 22 provided with an aperture at its center, and an objective lens 25. The illumination optical system for observation comprises an illumination light source 11 for observation such as a halogen lamp and a white light-emitting diode (LED), an infrared light transmission filter 12 which transmits only light within an infrared wavelength range (infrared light) of 750 nm or more, and a condenser lens 13, and the relay lens 18 to the objective lens 25.

The illumination optical system 10 doubles as a stimulating light irradiation optical system for irradiating the fundus Ef with visible stimulating light and stimulating a retina of the eye E in order to measure a retinal function of the eye E (the fundus Ef). For example, when measuring the retinal function, the light source 11 is lit, and the filter 12 is removed (retreated) from an optical path of the illumination optical system 10 (an illumination optical path) and a visible light transmission filter 90 which cuts (intercepts) light within an infrared range (infrared light) and transmits light within a visible range (visible light) is inserted into the illumination optical path. That is to say, the illumination optical system 10 comprises an inserting/removing mechanism 95 comprising a motor and other elements which selectively inserts and removes the filter 12 and the filter 90 into and from the illumination optical path. In the present embodiment of the present invention, the filter 90 has a property of transmitting only light within a visible range (visible light), for example, in the vicinity of green (e.g., λ=the vicinity of 568 nm).

The image-pickup optical system 30 comprises a fundus photographing optical system and a fundus observation optical system. The fundus photographing optical system comprises the objective lens 25, the apertured mirror 22, a diaphragm 31 placed in a position substantially conjugate with a pupil of the eye E, a focusing lens 32 or a focusing lens 102 which are movable in a direction of an optical axis of the image-pickup optical system 30, an image forming lens 33 or an image forming lens 103, and a two-dimensional image-pickup element 35 for photographing having sensitivity to a visible range. The fundus observation optical system comprises the objective lens 25 to the image forming lens 33 or the image forming lens 103, and a flip-up mirror 34 which is removed (retreated) from an optical path of the image-pickup optical system 30 (an image-pickup optical path) at the time of photographing the fundus Ef and is inserted into the image-pickup optical path at the time of observing the fundus Ef, a dichroic mirror 37 having a property of reflecting light within an infrared range (infrared light) and transmitting light within a visible range (visible light), an image-pickup lens 36, and a two-dimensional image-pickup element 38 for observation having sensitivity to an infrared range. That is to say, the image-pickup optical system 30 comprises a movement mechanism 49 comprising a motor and other elements which moves the focusing lens 32 or the focusing lens 102 in the optical axis direction and an inserting/removing mechanism 39 comprising a motor and other elements which selectively inserts and removes the flip-up mirror 34 into and from the image-pickup optical path.

The image-pickup optical system 30 doubles as an image-pickup optical system for performing normal color fundus photographing and an image-pickup optical system for performing retinal function measurement of the eye E (fundus Ef), and some of the constituent elements of the image-pickup optical systems are arranged to be switchable therebetween as usage. To be more specific, when picking up (obtaining) a normal color fundus image, an optical unit 301 which is a combination of the focusing lens (collimator lens) 32 having a short focal length and the image forming lens 33 having a long focal point is inserted into the image-pickup optical path so that a fundus image G1 is picked up largely over a photographable range C1 of the image-pickup element 35 as shown in FIG. 2A.

Meanwhile, when picking up (obtaining) a visible fundus image for the retinal function measurement, an optical unit 302 which is a combination of the focusing lens (collimator lens) 102 having a long anterior focal length and the image forming lens 103 having a short posterior focal point is inserted into the image-pickup optical path so that a fundus image G2 which is smaller than (one fifth the size of) the fundus image G1 is picked up in a photographing range C2 which is smaller than (one fifth the size of) the photographable range C1 of the image-pickup element 35 as shown in FIG. 2B. That is to say, the image-pickup optical system 30 comprises a placement switching mechanism 305 which selectively places either one of the optical unit 301 and the optical unit 302 on the image-pickup optical path. Besides, it is preferable that the image-pickup optical system 30 having the above-described configuration is optically designed so that the ranges of the fundus Ef images of which are to be taken become the same even if the optical systems (optical units) are switched as usage.

When picking up the normal color fundus image, the light source 11 is first lit and the fundus Ef is illuminated with infrared light via the filter 12. Reflection light from the fundus Ef illuminated with the infrared light is reflected by the flip-up mirror 34 via the optical unit 301 and is photo-received on the image-pickup element 38 (forms an image on an image-pickup plane of the image-pickup element 38). Output from the image-pickup element 38 is inputted into a calculation and control unit 80 and a monochrome fundus observation image (a fundus image for observation) picked up (obtained) by the image-pickup element 38 is displayed on a monitor (a display unit) 8.

When operations such as alignment (positional adjustment) and focusing (focus adjustment) are performed with the fundus observation image, the light source 14 is lit and the fundus Ef is illuminated with visible light. Reflection light from the fundus Ef illuminated with the visible light is photo-received on the image-pickup element 35 via the optical unit 301 (forms an image on an image-pickup plane of the image-pickup element 35). Output from the image-pickup element 35 is inputted into the calculation and control unit 80 and is stored in a memory (a storage unit) 85, and the color fundus photographed image (the normal color fundus image) picked up (obtained) by the image-pickup element 35 is displayed on the monitor 8.

The fixation target presenting optical system 70 comprises a fixation target light source (a fixation lamp) 74 such as a red light-emitting diode (LED), a relay lens 75 and the dichroic mirror 37, and the flip-up mirror 34 to the objective lens 25.

When the light source 74 is lit, visible light (red light) converges on the fundus Ef. Accordingly, the examinee (the eye E) fixates the light source 74.

The calculation and control unit 80 (hereinafter, referred to as a control unit 80) controls the whole of the apparatus and performs various kinds of calculation. The control unit 80 is connected with the light sources, the image-pickup elements 35 and 38, the inserting/removing mechanisms 39 and 95, the movement mechanism 49, the placement switching mechanism 305, a switch unit 84 having various kinds of switches, the memory 85, the monitor 8 and other elements. The switch unit 84 is provided with a focusing switch 84a for performing focusing of the fundus image, a mode selection switch 84b with which switching between a normal color fundus photographing mode (hereinafter, referred to as a fundus photographing mode) for picking up (obtaining) the normal color fundus image and a retinal function measurement mode of measuring the retinal function is performed, and other switches.

A calculation program for the retinal function measurement is prestored in the memory 85, and the control unit 80 obtains variance information which is used for the retinal function measurement by comparing the fundus images before and after irradiating the visible stimulating light.

The fundus camera according to the present preferred embodiment of the present invention further comprises an alignment mechanism (an optical system moving mechanism) which moves an optical axis (an image-pickup optical axis) L1 of the image-pickup optical system 30 three-dimensionally with respect to the eye E, a target projecting optical system and a target detecting optical system for performing alignment and other elements. However, an description of these elements is omitted since known configurations can be used for these elements and these elements have few relations with the present invention.

The normal color fundus photographing by the fundus camera having the above-described configuration and the retinal function measurement by the fundus camera having the above-described configuration are described separately.

<Normal Color Fundus Photographing>

When the fundus photographing mode is selected by operation of the switch 84b, the control unit 80 controls the light source 11 to light, and drives and controls the inserting/removing mechanism 95 to insert the filter 12 into the illumination optical path and to remove the filter 90 from the illumination optical path. In addition, the control unit 80 drives and controls the placement switching mechanism 305 to insert the optical unit 301 into the image-pickup optical path. Accordingly, the reflection light from the fundus Ef is photo-received on the image-pickup element 38.

Next, the apparatus is moved with respect to the eye E by operation of a joystick (not shown) or other control element, and alignment of the apparatus is performed so that a desired fundus observation image is displayed on the monitor 8. The focusing lens 32 is moved through driving and control of the driving mechanism 49 by operation of the switch 84a, and focusing is performed so that the desired fundus observation image is displayed on the monitor 8. When the desired fundus observation image is displayed on the monitor 8, a photographing button (not shown) is pressed.

When the photographing button is pressed, the control unit 80 controls the light source 14 to light, and drives and controls the driving mechanism 39 to remove the flip-up mirror 34 from the image-pickup optical path. Accordingly, the reflection light from the fundus Ef is photo-received on the image-pickup element 35. In this case, the fundus image G1 is picked up largely over the photographable range C1 of the image-pickup element 35 as shown in FIG. 2A. That is, the color fundus image under a predetermined image forming magnification S1 is formed on the image-pickup plane of the image-pickup element 35. The color fundus image is stored in the memory 85 and displayed on the monitor 8 as shown in FIG. 3A. The color fundus image picked up under the image forming magnification S1 is a fundus image picked up over the photographable range (the image-pickup plane) of the image-pickup element 35 and the number of pixels of the color fundus image used for a predetermined photographed area of the fundus Ef becomes larger, whereby a high-resolution and sharp color fundus image can be picked up (obtained).

<Retinal Function Measurement>

Meanwhile, when the retinal function measurement mode is selected by operation of the switch 84b, the control unit 80 controls the light source 11 to light and the monitor 8 to display the fundus observation image using the filter 12 and the optical unit 301 in an initial state similarly to the case where the fundus photographing mode is selected. When measuring the retinal function, it is preferable that the measurement is performed in a state where the eye E is dark adapted.

When the photographing button is pressed in a state where the desired fundus observation image is displayed on the monitor 8, the control unit 80 drives and controls the inserting/removing mechanism 95 to insert the filter 90 into the illumination optical path and to remove the filter 12 from the illumination optical path in order to pick up (obtain) the visible fundus image for the retinal function measurement. In addition, the control unit 80 drives and controls the placement switching mechanism 305 to insert the optical unit 302 into the image-pickup optical path, and drives and controls the driving mechanism 39 to remove the flip-up mirror 34 from the image-pickup optical path. Light from the light source 11 is irradiated onto the fundus Ef while an infrared range component of the light is cut by the filter 90 and a predetermined visible range component (e.g., a green component) of the light is transmitted through the filter 90.

In the present preferred embodiment of the present invention, the retinal function measurement is performed by detecting variance of brightness between the fundus images (images of the retina) using a photobleaching reaction of the retina. To be more specific, since when visible stimulating light (e.g., green light) is irradiated onto a fundus of an examinee's eye, a substance called rhodopsin contained in the retina is stimulated and a fading reaction occurs, reading the variance of brightness between the fundus images before and after the above-described retinal reaction allows variance of an intrinsic signal resulting from variance of activity of the substance in the retina to be obtained. Accordingly, the retinal function of the examinee's eye can be measured.

In the present preferred embodiment of the present invention, the visible stimulating light irradiated onto the fundus Ef via the filter 90 is also used as the visible illumination light for picking up (obtaining) the visible fundus image for the retinal function measurement. To be more specific, the reflection light reflected from the fundus Ef illuminated with the visible illumination light (the visible stimulating light) is photo-received on the image-pickup element 35 via the optical unit 302. Accordingly, the visible fundus image by the light source 11 and the filter 90 is picked up by the image-pickup element 35. In this case, light quantity of the light source 11 during the time that the filter 90 is inserted may be varied from light quantity of the light source 11 during the time that the filter 12 is inserted so that the visible light with suitable light intensity for the retinal function measurement is irradiated on to the fundus Ef.

In this case, the fundus image G2 is picked up in the photographing range C2 smaller than the photographable range C1 of the image-pickup element 35 as shown in FIG. 2B. To be more specific, the visible fundus image under a predetermined image forming magnification S2 (S2<S1) is formed on the image-pickup plane of the image-pickup element 35.

The control unit 80 picks up (obtains) the visible fundus images for the retinal function measurement by picking up over time the visible fundus images under the image forming magnification S2 based on an output signal from the image-pickup element 35. To be more specific, the control unit 80 controls the light source 11 to light continuously and the memory 85 to sequentially store the visible fundus images which are successively picked up at a frame rate of the image-pickup element 35 as the visible fundus images for the retinal function measurement. It is also preferable that the control unit 80 controls the light source 11 to flickeringly light and the memory 85 to sequentially store the visible fundus images which are picked up when the light source 11 is lit as the visible fundus images for the retinal function measurement. Alternatively, it is also preferable that the control unit 80 picks up the visible fundus image before the stimulation when the light source 11 is lit once, and picks up the visible fundus image after the stimulation when the light source 11 is lit again after a lapse of a predetermined period of time from turnoff of the light source 11. That is, the control unit 30 stores in the memory 85 a first visible fundus image and a second visible fundus image which are obtained from the same examinee's eye at different points in time (with staggered image-pickup timing).

As described above, since the illumination light source 11 for observation such as a halogen lamp and a white LED doubles as alight source for retinal stimulation and a light source for picking up (obtaining) the visible fundus image for the retinal function measurement, intensity of illumination light per unit time in illuminating the fundus Ef can be made lower than that in picking up (obtaining) the normal color fundus image. Therefore, faint light can be irradiated onto the fundus Ef, which prevents the photobleaching reaction of the retina from occurring rapidly, and continuous variance of the retinal reaction can be measured. In addition, by using a light source (e.g., a halogen lamp, a white LED) which emits light from a visible range to an infrared range as the illumination light source 11 and selectively inserting and removing the filter 12 and filter 90 into and from the illumination optical path, efficient pickup (obtainment) of the fundus observation image and efficient pickup (obtainment) of the visible fundus image for the retinal function measurement can be performed. Besides, it is also preferable to prepare an illumination optical system for picking up (obtaining) the visible fundus image for the retinal function measurement separately from an illumination optical system for picking up (obtaining) the color fundus image.

Incidentally, since the fundus image G2 under the image forming magnification S2 is a fundus image in the photographing range C2, the number of pixels of the fundus image G2 used for the predetermined photographed area of the fundus Ef becomes smaller than that of the fundus image G1 under the image forming magnification S1. In other words, a light-collecting action is exerted on the reflection light from the fundus Ef greater in a case where the optical unit 302 is placed on the image-pickup optical path than in a case where the optical unit 301 is placed on the image-pickup optical path, whereby photoreception efficiency per pixel can be increased. Thus, the variance of brightness of the fundus image made by the retinal stimulation can be detected at a high S/N ratio. Therefore, the variance of the intrinsic signal of the retina made by the retinal stimulation can be detected with high accuracy.

When the visible fundus image for the retinal function measurement is picked up (obtained) as described above, the control unit 80 shifts to the retinal function measurement subjected to calculation processing. The control unit 80 obtains variance information by comparing the first visible fundus image and the second visible fundus image which are stored in the memory 85. In this case, the control unit 80 obtains the variance of brightness between the fundus images made by the retinal stimulation for every pixel by using the fundus images before and after the retinal reaction to the visible stimulating light (the fundus images before and after the retinal stimulation) which are stored in the memory 85. For example, the control unit 80 obtains the variance of brightness of the fundus image for every pixel after a lapse of a predetermined period of time from the start of the stimulation from the brightness of the fundus image at the start of the stimulation by the visible light. The variance of brightness can be obtained by calculating a difference or a ratio between the fundus images. Then, the control unit 80 displays on the monitor 8 the obtained variance information of the brightness corresponding to each of the pixels as shown in FIG. 3B. The variance information of the brightness can be shown in a manner by which the variance information of the brightness is displayed as an image with a gradation or with a high-low brightness, or can be shown as numerical information of the difference or the ratio or as information obtained by subjecting the numerical information to the calculation processing using a given analysis program for evaluating the retinal function.

As described above, according to the above-described configurations, a sharp color fundus image suitable for a fundus examination can be picked up (obtained) and the retinal function can be measured with high accuracy.

Incidentally, in the above description, it is arranged that the image forming magnification on the image-pickup element 35 at the time of the retinal function measurement is optically switched (decreased) from the image forming magnification on the image-pickup element 35 at the time of the normal color fundus photographing by selectively placing the optical unit 301 for the normal color fundus photographing and the optical unit 302 for the retinal function measurement on the image-pickup optical path in accordance with the modes of the apparatus; however, the present invention is not limited thereto.

For example, a flip-up mirror capable of switching the optical paths may be provided in the image-pickup optical system 30, a first optical unit comprising a first image forming optical system with the image forming magnification S1 and a first image-pickup element may be provided on the transmitting side (the back side) of the flip-up mirror, and a second optical unit comprising a second image forming optical system with the image forming magnification S2 smaller than the image forming magnification S1 and a second image-pickup element may be provided on the reflection side of the flip-up mirror. In this case, when the flip-up mirror is flipped up, the first optical unit is used and the normal color fundus image is picked up (obtained). When the flip-up mirror is not flipped up, the second optical unit is used and the visible fundus image for the retinal function measurement is picked up (obtained). That is, it is essential only that the image forming magnification on the image-pickup element for the visible fundus image for the retinal function measurement be optically switched (decreased) from the image forming magnification on the image-pickup element for the normal color fundus image.

In addition, in the above description, while the image forming magnification on the image-pickup element 35 is optically switched, electrical means by which sensitivity (gain) of the image-pickup element 35 at the time of the retinal function measurement is switched (increased) from sensitivity (gain) of the image-pickup element 35 at the time of the normal color fundus photographing may be used. Alternatively, switching of the image forming magnification and switching of the sensitivity may be used in combination.

To be more specific, the gain of the output signal from the image-pickup element 35 is set lower when picking up (obtaining) the normal color fundus image while the gain of the output signal from the image-pickup element 35 is set higher when picking up (obtaining) the visible fundus image for the retinal function measurement. Hence, when picking up the normal color fundus image, an image-pickup signal is obtained in a state where background noise caused by the image-pickup element 35 is small. Accordingly, it is possible to pick up the color fundus image which is fine-grained and sharp. Meanwhile, when picking up the visible fundus image for the retinal function measurement, the photoreception efficiency of the image-pickup element 35 per pixel is increased and the variance of the intrinsic signal of the retina can be obtained at the high S/N ratio.

When performing the above-described gain adjustment, an image-pickup element having relatively high sensitivity such as image intensifier may be used as an image-pickup element. When picking up the visible fundus image for the retinal function measurement with image-pickup gain raised, the possibility that background noise increases is high. Therefore, it is preferable that noise removal processing such as median filter processing and averaging processing is performed. Meanwhile, when picking up the visible fundus image for the retinal function measurement with the image-pickup gain reduced, the background noise can be made smaller, whereby the fundus image which is realistic can be picked up. In this case, it is essential only that the first image-pickup element for the normal color fundus photographing and the second image-pickup element for the retinal function measurement be separately prepared and the sensitivity of the second image-pickup element be higher than that of the first imago-pickup element.

The present invention is not limited to the above-described manner, and when obtaining the variance information by comparing the first visible fundus image and the second visible fundus image, a plurality of fundus images which are picked up at different points in time and added together may be used as each of the visible fundus images. For example, comparison may be performed between the first visible fundus image which is obtained by adding fundus images obtained from the start of stimulation until a first predetermined time (e.g., 0 to 0.5 second) and the second visible fundus image which is obtained by adding fundus images obtained from the first predetermined time until a second predetermined time (e.g., 0.5 to 1.0 second).

When performing the normal color fundus photographing and the retinal function measurement on the same examinee's eye during the same period of time, the retinal function measurement is performed first and the color fundus photographing is performed later. This is in order to prevent photobleaching reaction from occurring due to light emission from a stroboscopic light source at the time of the color fundus photographing.

In the above description, while the retina is stimulated with the visible light using the light source 11 and the filter 90, the retina may be stimulated with visible flash light using the light source 14. In this case, the light quantity at the time of the retinal function measurement is decreased so as to be more than the light quantity at the time of the normal color fundus photographing by adjusting light quantity of the light source 14.

The control unit 80 may irradiate the fundus Ef with the light from the light source 14 during the interval between the pickup of the first visible fundus image and the pickup of the second visible fundus image which are performed at the different points in time (with staggered image-pickup timing). In this case, the color fundus image may be picked up by using the visible stimulating light irradiated onto the fundus Ef during the interval between the pickups of the visible fundus images before and after the stimulating light irradiation (including the time when the stimulation irradiation is started and the time after a lapse of the predetermined period of time from the start) as the visible illumination light. To be more specific, when a trigger signal by the photographing button is inputted, the control unit 80 picks up the first visible fundus image using the light source 11, the filter 90 and the optical unit 302, and then, picks up the color fundus image using the light source 14 and the optical unit 302 (with the filter 90 removed from the illumination optical path). Then, the control unit 80 picks up the second visible fundus image of the fundus Ef stimulated by the light emission from the light source 14 using the light source 11, the filter 90 and the optical unit 302.

Consequently, the retinal stimulation for the retinal function measurement and the normal color fundus photographing can be combined, which saves an examiner time and effort, and reduces a load on the examinee's eye imposed by the visible light irradiation.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:
an illumination optical system comprising a visible light source, for illuminating a fundus of an examinee's eye with visible light from the light source;
an image-pickup optical system comprising an image-pickup element, for photo-receiving reflection light from the fundus illuminated by the illumination optical system and picking up an image of the fundus;
a mode selection switch with which switching between a fundus photographing mode of picking up a normal color fundus image and a retinal function measurement mode of measuring a retinal function of the eye based on variance of an intrinsic signal of a retina of the eye made by retinal stimulation is performed; and
a control unit arranged to control the illumination optical system and the image-pickup optical system,
wherein the control unit lowers, when the retinal function measurement mode is selected, illumination intensity of the illumination optical system per unit time in illuminating the fundus by the illumination optical system than illumination intensity per unit time in picking up the color fundus image, and controls the image-pickup element to pick up a first visible fundus image and a second visible fundus image which are picked up at different points in time.

2. The fundus camera according to claim 1 further comprising:
an observation optical system comprising an image-pickup element for observing the fundus, for photo-receiving reflection light from the fundus illuminated with infrared light,
wherein the illumination optical system comprises a light source which emits light from a visible range to an infrared range and an inserting/removing mechanism which selectively inserts and removes an infrared light transmission filter which transmits the infrared light for the fundus observation and a visible light transmission filter which transmits the visible light for the retinal function measurement into and from an optical path of the illumination optical system.

3. The fundus camera according to claim 2 further comprising a photographing switch which is operated by an examiner,
wherein the control unit drives and controls the inserting/removing mechanism based on a signal from the photographing switch to insert the visible light transmission filter into the illumination optical path and remove the infrared light transmission filter from the illumination optical path.

4. The fundus camera according to claim 3, wherein the control unit varies the illumination intensity at the time when the visible light transmission filter is inserted from the illumination intensity at the time when the infrared light transmission filter is inserted.

5. The fundus camera according to claim 1, wherein the visible light source is a flash lamp which emits visible flash light and is used for the pickup of the color fundus image and for the retinal stimulation for the retinal function measurement.

6. The fundus camera according to claim 1, wherein the control unit sets, when the retinal function measurement mode is selected, gain of an image-pickup signal outputted from the image-pickup element to be higher than gain of the image-pickup signal outputted from the image-pickup element when the color fundus image is picked up in the fundus photographing mode.

7. The fundus camera according to claim 1, wherein the image-pickup optical system further comprises a first image-pickup element for picking up the color fundus image and a second image-pickup element for picking up a visible fundus image for the retinal function measurement, sensitivity of the second image-pickup element being higher than sensitivity of the first image-pickup element.

8. The fundus camera according to claim 1, wherein the image-pickup optical system further comprises;
- a first image forming optical system for forming a fungus image under a first imago forming magnification on the image-pickup element, the first image forming optical system being used in the fundus photographing mode; and
- a second image forming optical system for forming a fundus image under a second image forming magnification which is smaller than the first image forming magnification on the image-pickup element, the second image forming optical system being used in the retinal function measurement mode,
- wherein the first image forming optical system and the second image forming optical system can be selectively switched.

9. The fundus camera according to claim 8, wherein the image-pickup optical system further comprises a switching mechanism which selectively places the first image forming optical system and the second image forming optical system on an optical path of the image-pickup optical system.

10. The fundus camera according to claim 8,
- wherein the first image forming optical system comprises a first image-pickup element on which the fundus image is formed under the first image forming magnification,
- the second image forming optical system comprises a second image-pickup element on which the fundus image is formed under the second image forming magnification, and
- the image-pickup optical system further comprises a switching mechanism which selectively switches between an image-pickup optical path including the first image-pickup element and an image-pickup optical path including the second image-pickup element.

* * * * *